(12) United States Patent
Nakayama et al.

(10) Patent No.: US 7,875,850 B2
(45) Date of Patent: Jan. 25, 2011

(54) STANDARD COMPONENT FOR CALIBRATION AND ELECTRON-BEAM SYSTEM USING THE SAME

(75) Inventors: Yoshinori Nakayama, Sayama (JP); Yasunari Sohda, Kawasaki (JP); Keiichiro Hitomi, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 473 days.

(21) Appl. No.: 12/078,516

(22) Filed: Apr. 1, 2008

(65) Prior Publication Data
US 2008/0251868 A1 Oct. 16, 2008

(30) Foreign Application Priority Data
Apr. 11, 2007 (JP) .............................. 2007-103780

(51) Int. Cl.
*H01J 37/28* (2006.01)
*G01N 1/28* (2006.01)
*G01D 18/00* (2006.01)

(52) U.S. Cl. .................... 250/310; 250/307; 250/252.1; 257/48

(58) Field of Classification Search ................. 250/310, 250/307, 252.1
See application file for complete search history.

(56) References Cited

U.S. PATENT DOCUMENTS

| | | | |
|---|---|---|---|
| 5,847,468 | A | 12/1998 | Nomura et al. |
| 6,285,455 | B1 | 9/2001 | Shiraishi |
| 6,420,702 | B1 * | 7/2002 | Tripsas et al. ............... 250/310 |
| 6,916,743 | B2 | 7/2005 | Yamashita et al. |

(Continued)

FOREIGN PATENT DOCUMENTS

JP 8-153676 3/1995

(Continued)

OTHER PUBLICATIONS

Ichiko Misumi et al., "Technical Study of Nanometric Lateral Scale Consisting of GaAs/InGaP Superlattice" Development of Nanometric Lateral Scales (Second Report), National Institute of Advanced Industrial Science and Technology, pp. 1091-1092, and 10 pages of English translation.

*Primary Examiner*—Jack I Berman
(74) *Attorney, Agent, or Firm*—Stites & Harbison, PLLC; Juan Carlos A. Marquez, Esq.

(57) ABSTRACT

The invention provides a standard component for calibration that enables a calibration position to be easily specified in order to calibrate accurately a scale factor in the electron-beam system, and provides an electron-beam system using it. The standard component for calibration is one that calibrates a scale factor of an electron-beam system based on a signal of secondary charged particles detected by irradiation of a primary electron beam on a substrate having a cross section of a superlattice of a multi-layer structure in which different materials are deposited alternately. The substrate has linear patterns on the substrate surface parallel to the multi-layers and are arranged at a fixed interval in a direction crossing the cross section of the superlattice pattern, and the cross sections of the linear patterns are on substantially the same plane of the superlattice cross section, so that the linear patterns enable a position of the superlattice pattern to be identified.

13 Claims, 10 Drawing Sheets

U.S. PATENT DOCUMENTS 7,053,495 B2 5/2006 Tsuura
7,612,334 B2 * 11/2009 Nakayama et al. ....... 250/252.1
7,622,714 B2 * 11/2009 Yaguchi et al. .......... 250/252.1

FOREIGN PATENT DOCUMENTS

| JP | 2003-31484 | 7/2001 |
| JP | 2003-163268 | 8/2002 |
| WO | WO 99/27567 | 6/1999 |

* cited by examiner

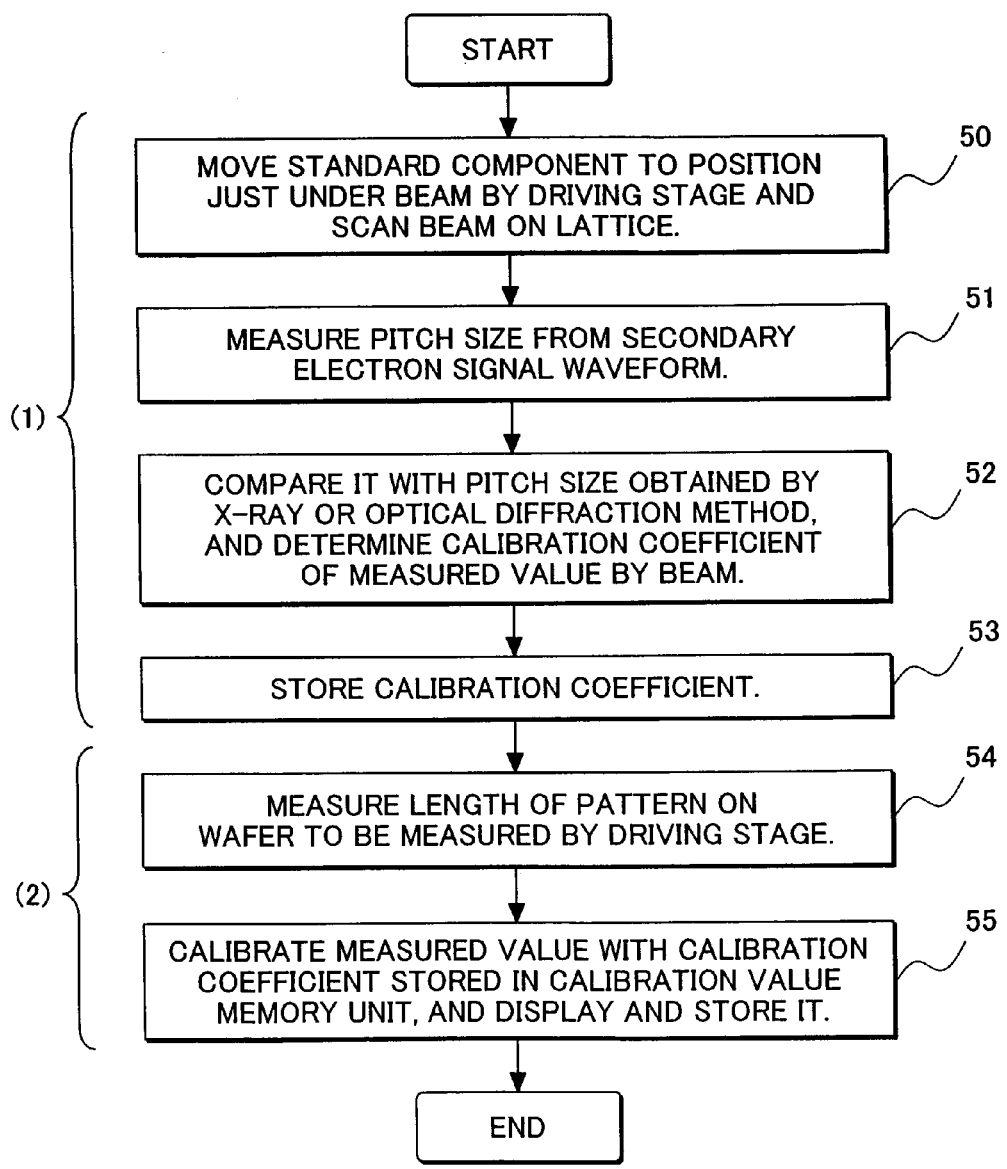

A-A' CROSS SECTION

STANDARD COMPONENT FOR CALIBRATION AND ELECTRON-BEAM SYSTEM USING THE SAME

The present invention claims priority from Japanese application JP 2007-103780 filed on Apr. 11, 2007, the content of which is hereby incorporated by reference on to this application.

BACKGROUND OF THE INVENTION

The present invention relates to a metrology calibration technology of an electron-beam system, and more specifically to a standard component for calibration in an electron-beam system, such as a high-accuracy electron-beam metrology system, used in a production process such as of semiconductor integrated circuits, and an electron-beam system using it.

In recent years, the semiconductor elements advance in microfabrication increasingly, and accordingly higher-accuracy metrology control management is needed. Therefore, in the field of semiconductor manufacture, metrology control management that uses an electron-beam metrology system based on the scanning electron microscope is practiced. Measurement accuracy of this metrology control management is determined by scale-factor calibration accuracy of the scanning electron microscope.

However, when higher scale-factor measurement is performed in response to microfabrication of semiconductor devices, because a visual field of the scanning electron microscope becomes a narrow area, a pattern of a standard component with which the scale-factor calibration is performed is required for minuteness comparable to or higher than semiconductor patterns. On the other hand, as a calibration component with minuteness of a pitch size of 100 nm or less, a superlattice sample as shown in Misumi et al., a paper No. 1091 of the Japan Society for Accuracy Engineering, Spring convention, Academic Lecture Meeting Technical Digest in 2006 fiscal year is proposed.

SUMMARY OF THE INVENTION

However, using a superlattice sample of the conventional technology as described above for scale-factor calibration of the electron-beam system has the following problems.

If a sample is irradiated with an electron beam, contamination adhesion will arise on the surface of the sample in a beam irradiation area, and the pattern will deform. Especially, in the superlattice sample with minuteness of 100 nm or less, because the samples is observed and measured under a high magnification of 100,000 or more, the beam dosage per area increases, and therefore contamination adhesion increases. For this reason, if the area subjected to a constant beam irradiation is used many times for calibration, the above-mentioned pattern deformation becomes large according to accumulated dosage and a basic linewidth will vary; therefore, the calibration accuracy will deteriorate. On the other hand, in order to identify a calibration area, consideration is needed that enables a position in a calibration pattern to be identified. However, since in a one-dimensional lattice pattern of the superlattice as described above, the line pattern is formed continuously in the whole cross section, the consideration for position identification is not done. For this reason, in the calibration of the electron-beam system, scale-factor calibration by the conventional technology has a problem that high-accuracy calibration such that a calibration position is located specifically in the beam-unirradiated part cannot be performed.

The object of the present invention is to provide a standard component for calibration with which it is easy to identify a calibration position in order to perform the scale-factor calibration accurately in the electron-beam system and to provide an electron-beam system using it.

The present invention solves the above-mentioned problem by forming a mark pattern (or labeled material) by which the calibration position is identified in proximity of a superlattice pattern (multi-layer structure pattern).

That is, the standard component for calibration is on a substrate having a cross section of a superlattice pattern of a multi-layer structure in which different materials are deposited alternately, has linear patterns arranged at a fixed interval in a direction crossing the cross section of the superlattice pattern on the substrate surface parallel to the superlattice pattern, and is so configured that the cross section of the linear patterns may exist on substantially the same plane of the superlattice cross section, so that the linear patterns enable a position of the superlattice pattern to be identified, as a fundamental structure.

By adopting such a configuration, in the present invention, a position of the superlattice pattern linearly continuous in a one-dimensional direction can be identified easily, and therefore secure positioning becomes possible regardless of accuracies of a stage and beam deflection of the electron-beam system to be calibrated. Moreover, the configuration enables calibration that controls the number of use using a desired superlattice pattern area. Furthermore, the above-mentioned calibration becomes possible irrespective of positioning accuracy of the electron-beam metrology system to be calibrated.

Still moreover, as the standard component for the electron-beam system, a formed mark is required to be one that gives sufficient contrast on a secondary charged particle (secondary electron, reflected electron, etc.) image by electron beam irradiation.

Therefore, in a calibration position identification mark pattern of the present invention, by the mark using a metal material, such as aluminum (Al), tungsten (W), tantalum (Ta), molybdenum (Mo), and copper (Cu), especially a heavy metal, the mark is free from electrification and can obtain a secondary electron signal whose contrast is high to the superlattice substrate, and therefore detection accuracy of the mark becomes high.

Moreover, as the calibration position identification mark of the present invention, a mark whose number of mark elements or shape is changed correspondingly to the position coordinates of each pattern unit or the like is considered.

Moreover, when forming the mark in proximity of the superlattice pattern, a method for etching the mark on the substrate after formation of the superlattice cross section by etching, such as ion beam etching, is considerable. However, in this process, since residual after etching etc. adheres to the superlattice pattern for calibration, there is a risk of pattern deformation. Therefore, it is desirable, according to a method for producing a standard component for calibration of the present invention, that the calibration position identification mark pattern is formed in advance in a process before the formation of the cross section.

Moreover, since the mark is made up of linear patterns arranged at a constant interval in a direction crossing a cross section of the substrate on a surface of the multi-layer; when making a whatever cross section, if the linear patterns cross the cross section, a desired mark pattern can be formed easily in a multi-layer cross section of the superlattice sample. Moreover, by changing the number of constituent mark elements and/or by altering a size and a cross section thereof, a different mark pattern from the adjacent mark patterns can be formed.

Furthermore, it is possible to adjust a cut-out position of the cross section with high accuracy by using these marks and by a sample cutting process using an ion beam. Still moreover, if a pitch size of the linear patterns that are arranged at a fixed interval in a direction crossing the surface of the multi-layer is obtained by optical measuring means, calibration of a linewidth in a direction perpendicular to the multi-layer interval of the superlattice will become possible.

According to the present invention, the standard component for calibration that makes it easy and with high accuracy to select the superlattice pattern used for calibration is realized and an electron-beam system using it is realized further.

BRIEF DESCRIPTION OP THE DRAWINGS

FIG. 5 is a diagram showing a flow of a calibration method by the present invention;

FIGS. 6A and 6B show a superlattice multi-layer wafer with a calibration position identification mark; wherein FIG. 6A is a top view thereof and FIG. 6B is an A-A' cross section thereof;

DETAILED DESCRIPTION OF THE PREFERRED EMBODIMENTS

Hereafter, embodiments of the present invention will be explained in detail with reference to the drawings.

First Embodiment

In this embodiment, explanation will be given to a structure example of a standard component for calibration used for an electron-beam metrology system (CD-SEM or electron-beam metrology system) as the electron-beam system, including an embodiment in the case of actually using that standard component in the electron-beam metrology system.

Figure 1:
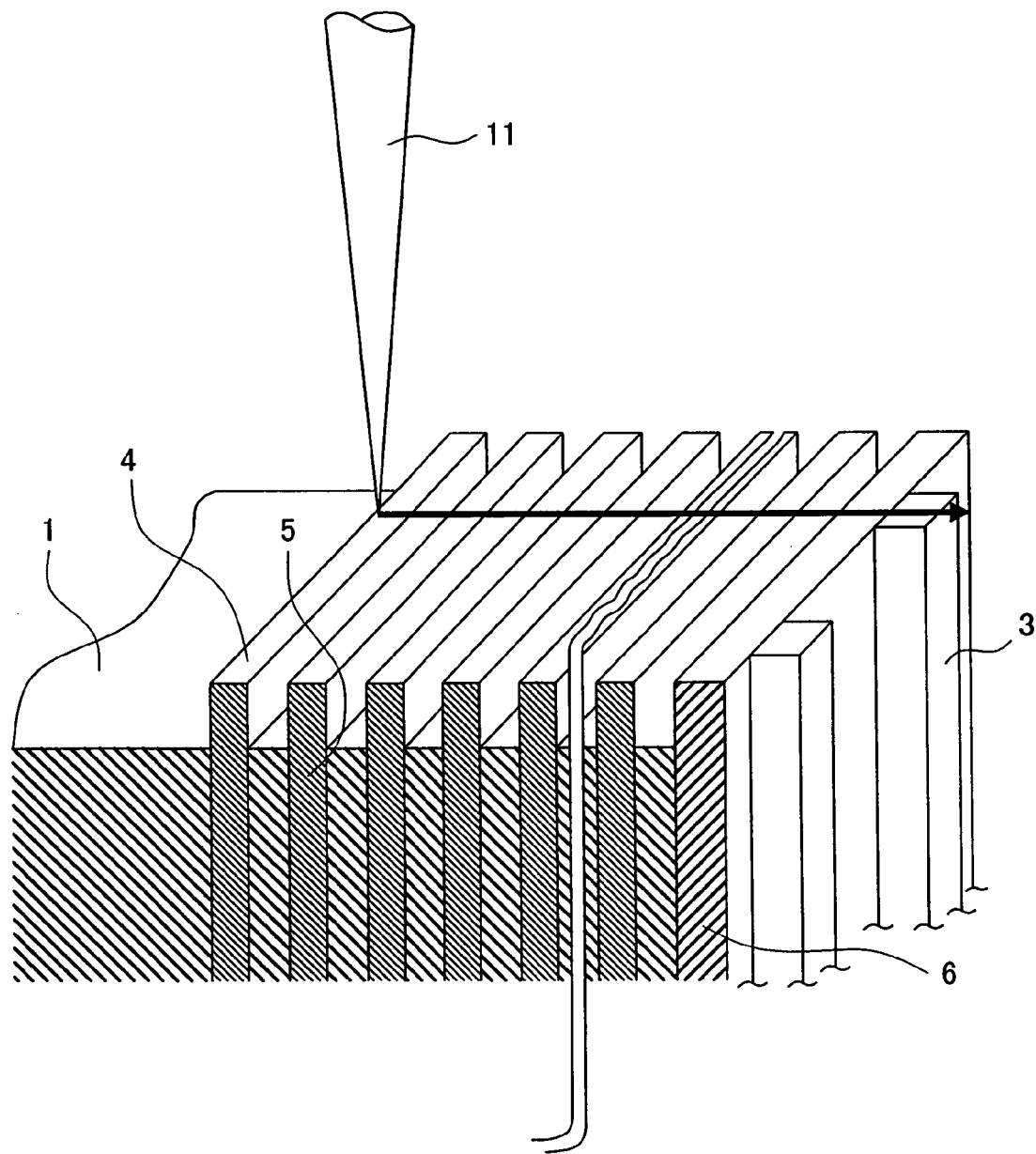
FIG. 1 is a diagram showing an appearance of a standard component for calibration of one embodiment of the present invention.
Figure 2:
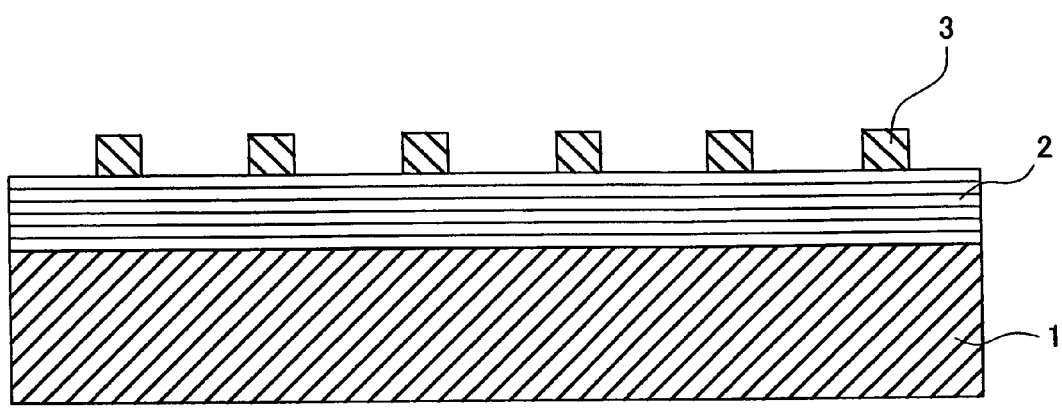
FIG. 2 is a top view viewed from a scanning surface side of the standard component for calibration shown in FIG. 1.

FIG. 1 is an external view of the standard component for calibration of this embodiment, and FIG. 2 shows a top view viewed from the electron-beam scanning surface side of the standard component for calibration shown in FIG. 1.

The standard component for calibration shown in FIG. 1, 2 has a structure where a superlattice-for-calibration multi-layer film formation area 2 and a calibration position identification mark 3 are formed on a substrate 1 made up of a silicon wafer in a rectangular shape. The calibration position identification mark 3 is formed on a surface of the substrate in the superlattice-for-calibration multi-layer film formation area 2. Incidentally, an arrow in the figure shows a scanning direction of a primary electron beam at the time of calibration.

In the superlattice-for-calibration multi-layer film formation area 2, a molybdenum (Mo) layer 4 and a silicon (Si) layer 5 each 12.5-nm thick are deposited repeatedly 40 times at a pitch interval of 25 nm to form a multi-layer, and on its surface, a silicon carbide (SiC) layer 6 is deposited to 15 nm. The Si layer 5 in this multi-layer is etched to a depth of 50 nm by material selected etching. Regarding the pitch interval of the Mo layer 4 and the Si layer 5 of this sample, 25.01 nm found by the X-ray diffraction method is obtained as an absolute pitch size.

On a surface of the multi-layer, calibration position identification marks 3 are arranged repeatedly 10000 times at a pitch interval of 200 nm, each having a rectangular cross section of a length of 1 mm, a width of 50 nm in a depth direction, and a height of 50 nm. Regarding the pitch interval of a rectangular cross section of this calibration position identification mark 3, 200.09 nm found by a diffraction method with ultraviolet light is obtained as an absolute pitch size.

Next, a method for calibrating an electron-beam metrology system (CD-SEM) using the standard component for calibration of this embodiment will be explained.

Figure 3:
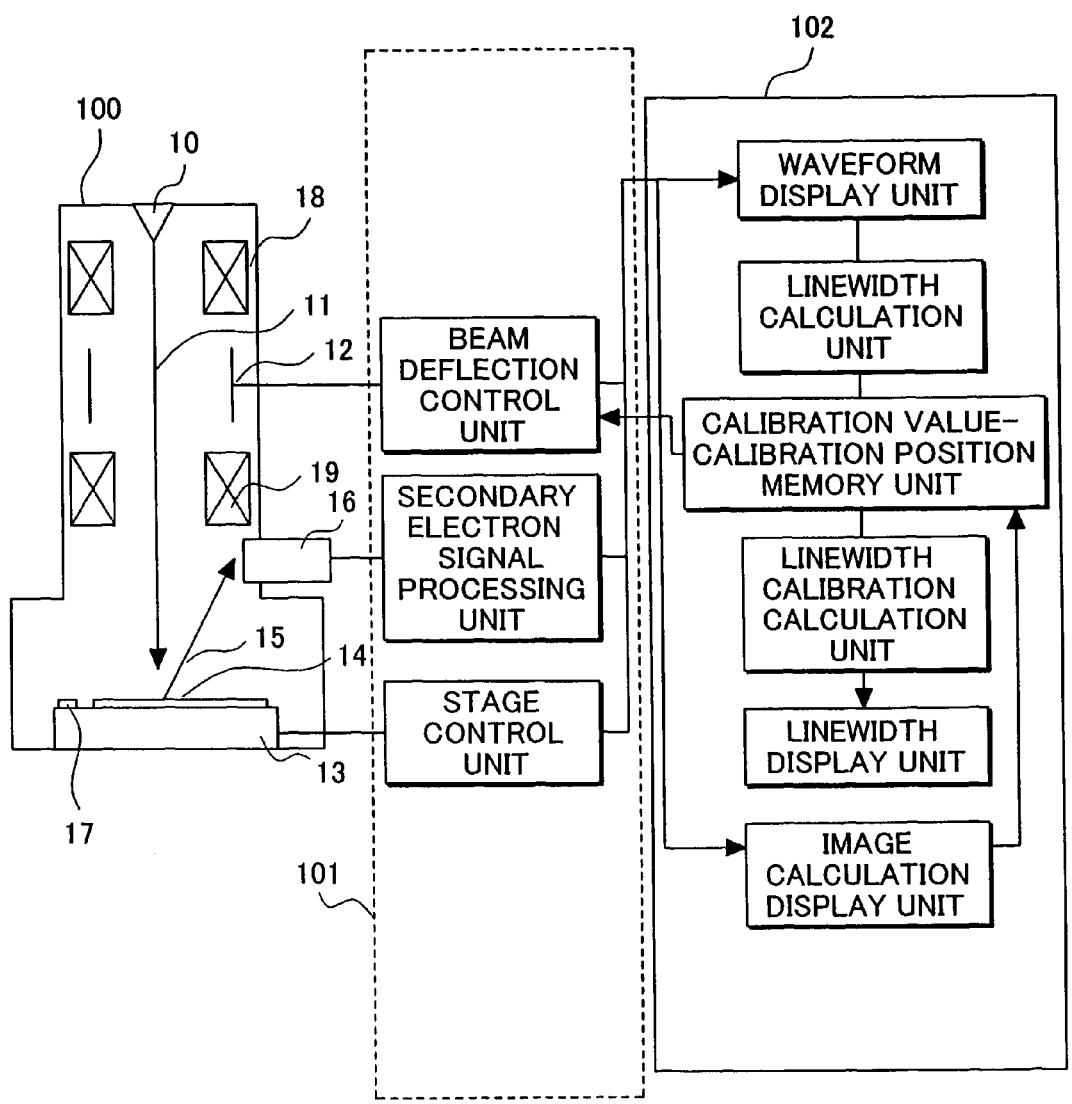
FIG. 3 is a diagram for explaining an electron-beam metrology system that uses the standard component for calibration of the present invention.
Figure 4:
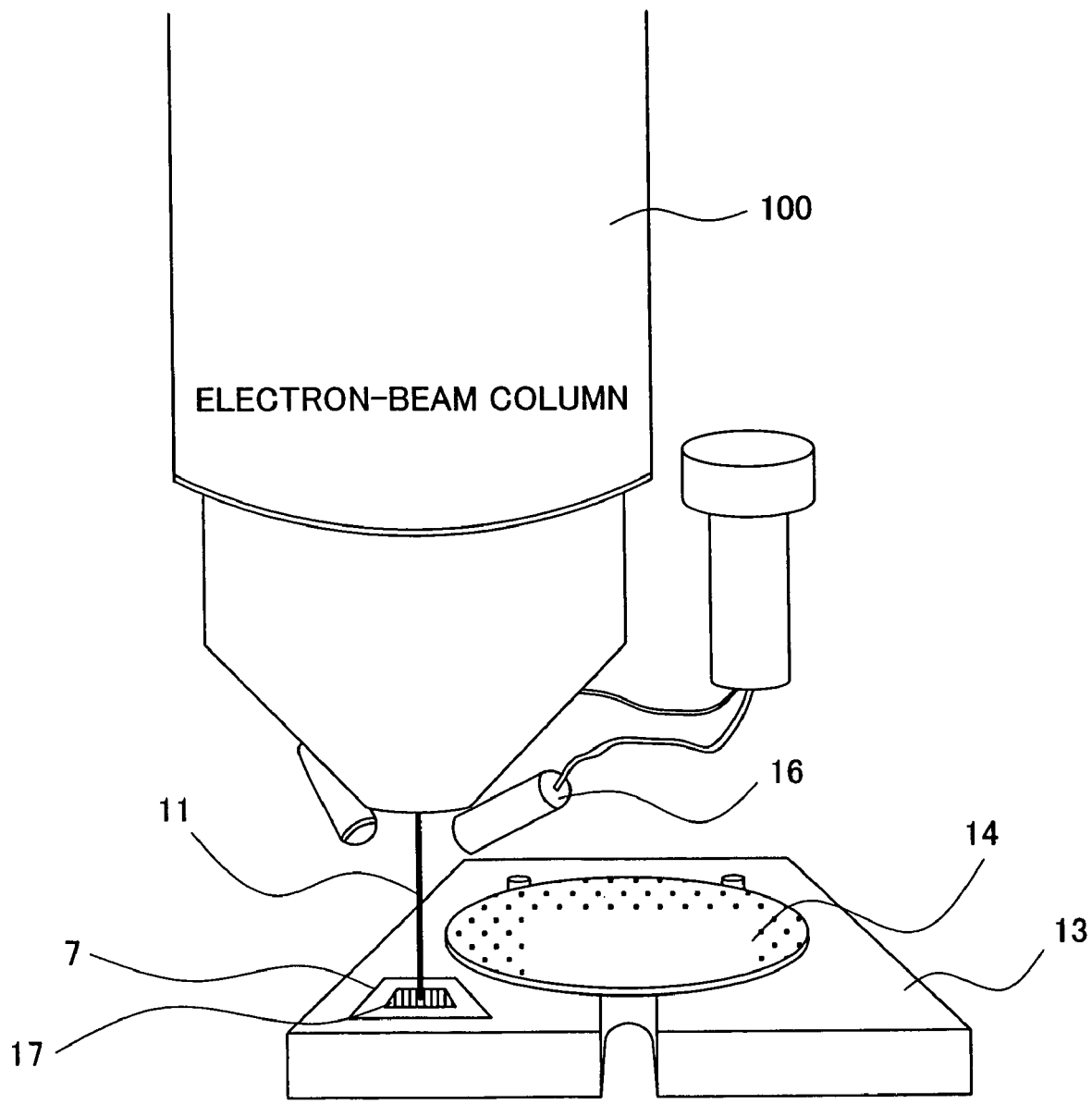
FIG. 4 is a schematic diagram near a sample stand in the electron-beam metrology system shown in FIG. 3.

FIG. 3 is a diagram showing a whole configuration of the CD-SEM in which the standard component for calibration of this embodiment is used, and FIG. 4 is a schematic diagram showing a placement position of the standard component for calibration and the relation between a placement position of the sample subjected to metrology and an irradiation position of the primary electron beam.

The electron-beam metrology system shown in FIG. 3 is constructed with an electron-beam column 100, an SEM control unit 101, an information processor 102, etc. The electron-beam column 100 includes an electron gun 10 for emitting a primary electron beam 11, a scanning deflector 12 for scanning the primary electron beam 11 onto a sample subjected to metrology, lenses 18, 19 for adjusting focusing of the electron beam on the sample subjected to metrology, a secondary electron detector 16 for detecting secondary electrons or reflected electrons 15 generated by irradiation of the primary electron beam 11.

The SEM control unit 101 is constructed with a beam deflection control unit for controlling scanning deflection of the primary electron beam, a secondary electron signal processing unit for processing an output signal from the secondary electron detector, a stage control unit for controlling a stage 13 on which a sample 14 subjected to metrology or a standard component 17 for calibration is placed and held, etc.

The information processor 102 includes a signal wave display unit form display for displaying each information inputted from the SEM control unit 101 or a signal waveform obtained form a control signal, a calibration value-calibration position memory unit for storing a calibration coefficient of the system, a position, a defect, and the number of use of the standard component used for calibration, a linewidth calibration calculation unit for calculating an actual linewidth from these calibration coefficients, a linewidth display unit for displaying the obtained actual linewidth, and an image calculation display unit for analyzing and displaying a secondary electron or reflected electron image.

Incidentally, the electron-beam metrology system includes other indispensable constituents that are not illustrated in FIG. 3 as components thereof.

Moreover, in this example, the standard component 17 for calibration that is mounted on a holder 7 made of aluminum and the sample 14 subjected to metrology are placed and held on the same stage 13, as shown in FIG. 4.

FIG. 5 shows an operation flow of the CD-SEM at the time of calibrating metrology data. The flow of FIG. 5 is divided roughly into (1) a calibration-coefficient determination flow of metrology data using the standard component (Steps 50, 51, 52, and 53), and (2) an acquisition and calibration flow of the metrology data (Steps 54 and 55).

First, the standard component 17 for calibration is moved at the irradiation position of the primary electron beam by driving the stage, and a predetermined area is scanned by the primary electron beam 11 as shown by an arrow in FIG. 1 at approximately a scale factor at which the superlattice-for-calibration multi-layer film formation area 2 and the calibration position identification mark 3 shown in FIG. 2 are included. Obtained pixel information is analyzed by the image calculation display unit, whereby a position coordinate labeled material corresponding to the superlattice-for-calibration multi-layer film formation area 2 existing on an optical axis of the primary electron beam is identified. In controlling the stage, proper origin initialization is done between the coordinate system of the standard component and the coordinate system of the stage controlling, and coordinate information in the coordinate system of the standard component 17 for calibration is converted into coordinate information in the coordinate system of stage controlling. The origin initialization for coordinate conversion is performed at an appropriate frequency, for example, each time the stage 13 on which the standard component 17 for calibration is placed and held is carried into and carried out from a vacuum vessel.

Moreover, the calibration value-calibration position memory unit stores use frequency information of the superlattice-for-calibration multi-layer film formation area 2 corresponding to each set of position coordinates and a threshold of the number of use. Furthermore, the calibration value-calibration position memory unit also stores information as to whether the superlattice-for-calibration multi-layer film formation area 2 corresponding to each position coordinate labeled material includes a defect.

The identified superlattice-for-calibration multi-layer film formation area 2 is collated with calibration history and defect position information in the calibration value-calibration position memory unit, and is checked in terms of whether a defect exists, whether the number of use exceeds a stipulated number of use, etc. Check items, for example, information of the threshold of the number of use, the superlattice multi-layer film formation area that is not used, etc. is set up by the information processor 102. If the identified superlattice multi-layer film formation area fulfills the check items, an acquisition flow of the calibration coefficient will be performed using the current superlattice multi-layer film formation area. If it does not fulfill, another suitable superlattice multi-layer film formation area is selected.

For example, assume as follows: position coordinates of the calibration position identification mark 3 that is moved onto the optical axis of the primary beam by the first stage movement and the superlattice-for-calibration multi-layer film formation area 2 are recognized, and checking by the image calculation display unit and the calibration value-calibration position memory unit shows that the superlattice-for-calibration multi-layer film formation area corresponding to this position coordinates has no defect but was used about 10 times in the past for pitch measurement by beam irradiation. Then, by referring to information stored in the image calculation display unit and the calibration value-calibration position memory unit, position coordinates of the superlattice-for-calibration multi-layer film formation area nearest to the superlattice-for-calibration multi-layer film formation area that fulfills check items is calculated. Furthermore, the image calculation display unit calculates the amount of movement of the stage or the amount of beam deflection necessary to move the beam irradiation position to the calculated superlattice-for-calibration multi-layer film formation area and transfers it to the SEM control unit 101. The SEM control unit 101 controls a stage drive device or the scanning deflector 12 based on the transferred information and moves the superlattice-for-calibration multi-layer film formation area that should be used to a scanning range of the primary electron beam (Step 50).

After the movement of the superlattice-for-calibration multi-layer film formation area to be used is completed, a magnification is changed to a high magnification (a magnification such that the superlattice-for-calibration multi-layer film formation area 2 shown in FIGS. 1, 2 expands all over the visual field), and the superlattice-for-calibration multi-layer film formation area is actually scanned by the beam. In the beam scanning, focus adjustment of the electron-beam column 100 is performed. The focus adjustment is done by adjusting electron optics system lenses 18, 19 provided in the electron-beam column 100. In this embodiment, in order to reduce unnecessary beam irradiation to the superlattice multi-layer film formation area as less as possible, the calibration position identification mark 3 is used to perform the focusing. However, naturally, it is also possible to perform the focusing by irradiating the superlattice-for-calibration multi-layer film formation area with the primary electron beam.

After completion of the focus adjustment, a predetermined area is scanned with the beam, an obtained secondary electron signal waveform is subjected to signal processing, and a pitch size of the superlattice-for-calibration multi-layer film formation area is found by a linewidth calculation unit (Step 51).

The calibration value-calibration position memory unit stores an absolute pitch size of 25.01 nm obtained by an X-ray diffraction method, and the linewidth calibration calculation unit calculates the calibration coefficient by comparing the pitch size calculated by the linewidth calculation unit with the absolute pitch size stored in the calibration value-calibration position memory unit (Step 52).

The obtained calibration coefficient is stored in the calibration value-calibration position memory unit. Moreover, the position coordinates of the superlattice-for-calibration multi-layer film formation area that was used for calibration and the number of use of the superlattice multi-layer film formation area are stored in the calibration value-calibration position memory unit. Furthermore, that the calibration coefficient was normally acquired is displayed on the display unit (Step 53).

Incidentally, if a foreign matter or defect is found in the area subjected to beam scanning, coordinates corresponding to the superlattice multi-layer film formation area are stored in the calibration value-calibration position memory unit, the processing returns to the start of the flow, and a selection operation of an appropriate superlattice multi-layer film formation area is performed.

Next, a flow of FIG. 5 (2) will be explained. It is configured that, when the flow of the above (1) completes normally, the stage 13 is moved so that a desired pattern on the wafer 14 may be moved to the irradiation position of the primary electron beam 11. Generated secondary electrons 15 are detected by the secondary electron detector 16 and the signal is inputted into the information processor 102 as a secondary electron signal. In an image calculation-display unit, position information of an edge point of a pattern subjected to metrology is extracted from the inputted secondary electron signal, and is transferred to the linewidth calculation unit. The linewidth calculation unit calculates a pattern linewidth from obtained position information of the edge point, and transfers it to the linewidth calibration calculation unit (Step 54).

The linewidth calibration calculation unit corrects the measured value using the calibration coefficient obtained by the above-mentioned flow (1). Further, the measured value after the correction is outputted to the display 114, and is displayed thereon (Step 55).

As a result of correction of the measured value using the calibration component of this embodiment, metrology accuracy of 0.2 nm or less has been realized to the pattern linewidth of 50 nm.

Incidentally, in the above explanation of FIG. 5, although it was explained that the system performed automatically the flow in response to a request of the system user in the above flow (1) and (2), it is also possible for the system user to execute each step included in the flow by a manual operation. Even in that case, since the calibration position identification mark 3 has been given to each superlattice multi-layer film formation area, identification of the position coordinates in the superlattice-for-calibration multi-layer film formation area 2 is easy as compared to that by the conventional technology, and accurate calibration is realized regardless of accuracy of stage position control.

Moreover, in the above explanation, although focus adjustment of the primary electron beam was performed on the calibration position identification mark in order to reduce contamination probability in the superlattice multi-layer film formation area, on the contrary, a recipe may be set up so that the superlattice multi-layer film formation area corresponding to the same calibration position identification mark may be always used. By monitoring a variation of the pitch size that is measured using the superlattice multi-layer film formation area at the same position, temporal variation of contamination can be observed. In that case, a functional block for storing the measured value of the pattern linewidth and the number of use of a specific superlattice multi-layer film formation area in pairs is provided in memory in the calibration value-calibration position memory unit shown in FIG. 4.

Moreover, by performing calibration to a plurality of electron-beam metrology system using the superlattice multi-layer film formation area of the same calibration position identification mark, it becomes possible to perform calibration between systems with the same standard; therefore, it becomes possible to grasp a difference of metrology performance between the plurality of systems (namely, instrumental error) more accurately than before.

However, in the electron-beam metrology system, within an SEM visual field, only of the line patterns in the same direction are not always subjected to metrology, or rather, there is a possibility that both of lines whose longitudinal direction points in the X-direction and lines whose longitudinal direction points in the Y-direction are subjected to metrology. Although the system is calibrated using the interlayer pitch size of the superlattice multi-layer film formation area 2 in the above-mentioned example, it is possible to perform the system calibration using the pitch size between the patterns of the calibration position identification mark 3 according to the same approach. That is, the linewidth calculation unit finds the pitch size between the patterns of the calibration position identification mark 3 by scanning the plurality of calibration position identification mark 3 areas that are predetermined and signal-processing the obtained secondary electron signal waveform. The calibration value-calibration position memory unit stores 200.09 nm obtained by a diffraction method with ultraviolet light as an absolute pitch size, and the linewidth calibration calculation unit calculates the calibration coefficient by comparing the pitch size calculated by the linewidth calculation unit with the absolute pitch size stored in the calibration value-calibration position memory unit. The obtained calibration coefficient is stored in the calibration value-calibration position memory unit. The position coordinate labeled material of a calibration position identification mark area used for the calibration and the number of use of the calibration position identification mark area are stored in the calibration value-calibration position memory unit. Moreover, that the calibration is normally acquired is displayed on the image calculation-display unit and the linewidth display unit.

Incidentally, if a foreign matter or defect is found in the area subjected to beam scanning, position coordinates corresponding to the calibration position identification mark 3 area will be stored in the calibration value-calibration position memory unit, and the processing will return to the beginning of the flow and execute a selection operation of an appropriate calibration position identification mark 3 area.

As a result, metrology calibration in the perpendicular direction is attained with metrology accuracy of 0.5 nm or less to the interlayer pitch size of the superlattice multi-layer film formation area.

As described in the foregoing, the use of the standard component for calibration and the electron-beam metrology system of this embodiment realizes the metrology system that selects and confirms the superlattice multi-layer film formation area easily and is capable of always stable calibration without being affected by linewidth variation by contamination and the defect of the lattice, and also realizes a metrology method and a standard component for calibration. Incidentally, although in this embodiment, an example where the standard component for calibration is applied to the electron-beam metrology system was explained, it is natural that it can be applied to scanning-electron-microscope application apparatuses, such as the general-purpose SEM and the inspection SEM.

Second Embodiment

Figure 6A:
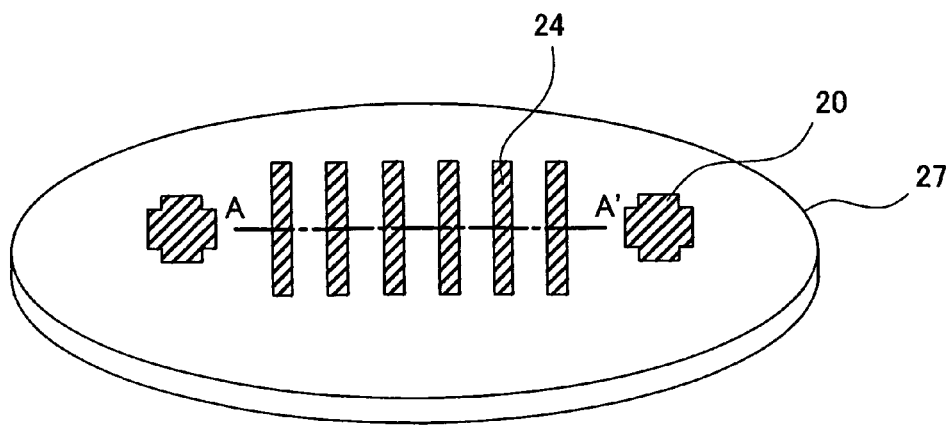
Figure 6B:
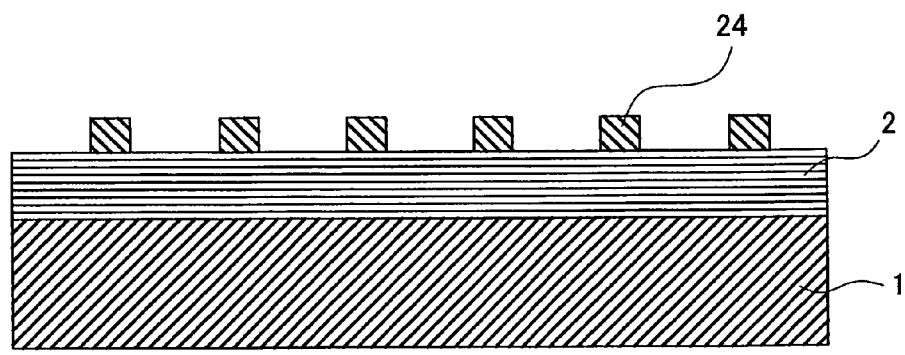
Figure 7:
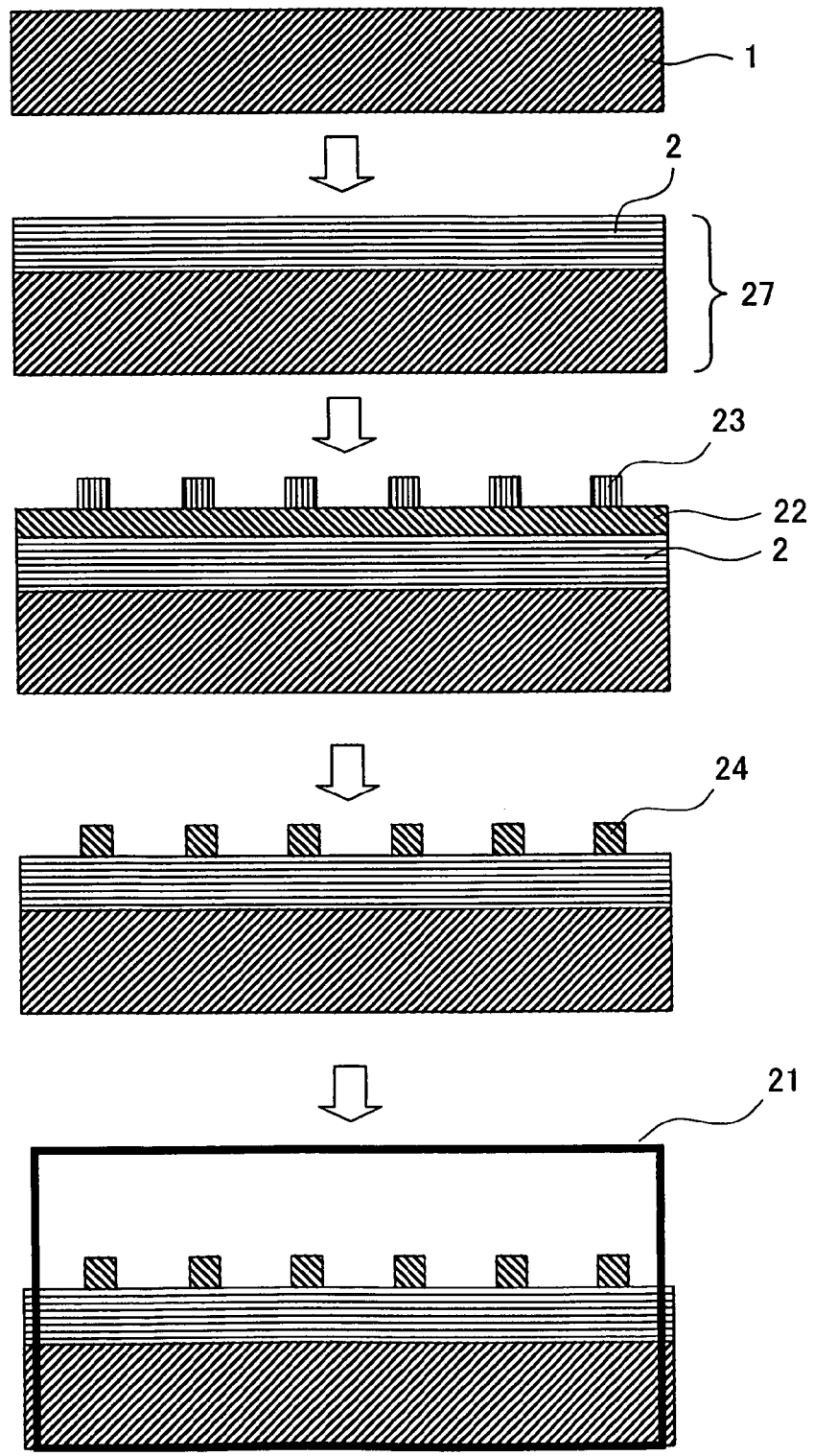
FIG. 7 is a cross section in production process steps of the standard component for calibration of the present invention.

In this embodiment, a method for producing a standard component with the calibration position identification mark of the present invention shown in FIG. 1 will be described with reference to FIGS. 6, 7, and 8. FIG. 6A shows a top view of a whole surface of a superlattice multi-layer wafer for calibration with a calibration position identification mark pattern, and FIG. 6B shows its A-A' cross section. FIG. 7 is cross sections in the production process steps of the standard component for calibration of the present invention, and FIG. 8 shows a production process flow of the standard component for calibration.

Figure 8:
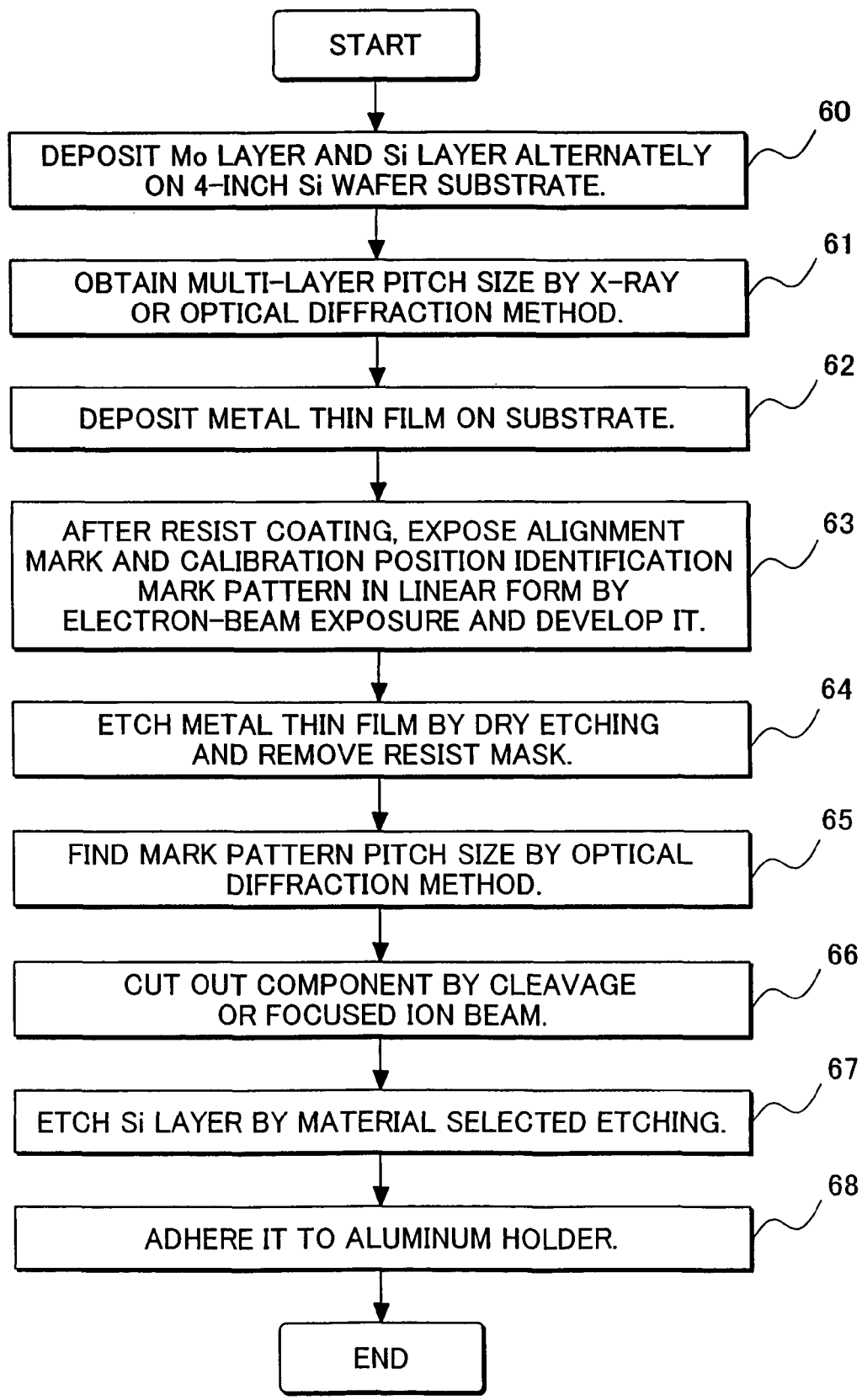
FIG. 8 is a diagram showing a production process flow of the standard component for calibration of the present invention.

First, on the surface of the substrate 1 of the 4-inch Si wafer shown in FIGS. 6A, 6B and FIG. 7, the Mo layer 4 and the Si layer 5 each 12.5 nm thick are deposited alternately repeatedly 40 times at a pitch interval of 25 nm, and on the surface thereof a SiC layer 6 is deposited to 15 nm to form the superlattice-for-calibration multi-layer film formation area 2 as a superlattice multi-layer substrate 27, as shown in FIG. 1 (FIG. 8, Step 60).

The multi-layer pitch interval of this multi-layer substrate 27 is obtained by an X-ray diffraction apparatus (FIG. 8, Step 61).

A 50 nm thick tungsten thin film 22 is further formed on the surface of this superlattice multi-layer substrate 27 by sputtering (FIG. 8, Step 62).

After coating a resist layer on this tungsten thin film with a spin coater, a linear resist pattern 23 of a length of 1 mm, a width of 50 nm, and a height of 100 nm is formed repeatedly 10000 times at a pitch interval of 200 nm by electron beam exposure and development. Simultaneously, a cross mark resist pattern for alignment of a length of 0.6 mm, a width of 0.2 mm, and a height of 100 nm was formed around the perimeter of the above-mentioned linear resist pattern group by the same electron beam exposure and development (FIG. 8, Step 63).

After etching the tungsten thin film of 50 nm thickness by dry etching using these resist patterns as a mask, the resist is removed by ashing. A pattern group in which a linear tungsten pattern 24 of 1 nm length, 50 nm width, and 50 nm height is repeated 10000 times at a pitch interval of 200 nm and a cross mark tungsten pattern 20 for alignment of a length of 0.6 mm, a width of 0.2 mm, and a height of 50 nm are formed (FIG. 8, Step 64).

After this, the pitch interval of the linear tungsten pattern 24 is found by an optical diffractometer (FIG. 8, Step 65).

Next, with respect to the cross mark tungsten pattern 20 for alignment of the 4-inch multi-layer wafer 27, the linear tungsten pattern 24 is cleaved in a perpendicular direction. Further, it is cleaved in a direction parallel to the linear tungsten pattern 24, and an area 21 shown in FIG. 7 by a black rim is cut out (FIG. 8, Step 66).

In doing this, although an optical microscope was used to check a cut-out position an optical microscope image high-contrast to the surface SiC layer 6 of FIG. 1 was attained because the linear tungsten pattern 24 and the cross mark tungsten pattern 20 for alignment are both of metal, which enables easy position determination. The accuracy of the cut-out position was approximately 1 mm.

The Si layer of the standard component sample with the calibration position identification mark that was cleaved is etched to a depth of 50 nm by alkaline water solution, such as of TMAH (trimethylammoniumhydride). This process yields the standard component 17 with the calibration position identification mark of the present invention having a cross section structure as shown in FIG. 1 (FIG. 8, Step 67). This member is mounted on (or adhered to) the holder 7 made of aluminum to complete the standard component (FIG. 8, Step 68), which is mounted on the stage 13 of the electron-beam system to perform the calibration.

In the above-mentioned sample cutting-out, as a cutting-out method better than the cleave method in terms of identification of a cut-out location and linearity, cutting-out by a focused ion beam is effective.

Figure 9:
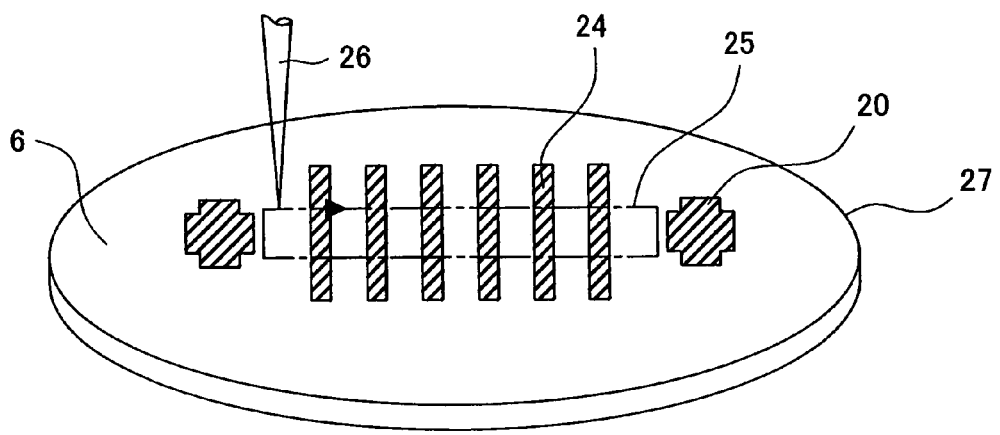
FIG. 9 is an outline diagram showing one example of a process of cutting out the superlattice multi-layer wafer with the calibration position identification mark of the present invention.

In this case, as shown in FIG. 9, a cut-out area is scanned by a focused ion beam 26, and the linear tungsten pattern 24 and the cross mark tungsten pattern 20 for alignment are checked with its secondary ion image. In this case, since the each pattern is formed with a conductive and heavy metal, the secondary ion image having high-contrast to the surface SiC layer 6 is obtained, and the cut-out position can easily be determined.

Using the secondary ion image of this cross mark tungsten pattern 20 for alignment as a reference, the focused ion beam 26 is deflected and scanned in a perpendicular direction and parallel direction to the linear tungsten pattern 24 to cut out a cut-out area of a dotted line part 25. Processing after cutting-out is the same as that of the above-mentioned process. Accuracy of the cut-out position by this method was 10 µm or less.

Although in the above-mentioned example, tungsten was used as a mark material by way of example, the same effect can be obtained when a metal material, such as aluminum (Al), tantalum (Ta), molybdenum (Mo), and Copper (Cu), is used.

Third Embodiment

In this embodiment, another example of the calibration position identification mark of the standard component for calibration that was explained in the first embodiment will be described.

In the superlattice-for-calibration multi-layer film formation area 2 of the standard component for calibration of the first embodiment, as shown in FIGS. 1, 2, the Mo layer and the Si layer each 12.5 nm thick are deposited repeatedly 40 times at a pitch interval of 25 nm. The Si layers in this multi-layer are etched to a depth of 50 nm by material selected etching. Regarding the pitch interval of the Mo layer and the Si layer of this sample, 25.01 nm found by an X-ray diffraction method is obtained as an absolute pitch size. On the surface of the multi-layer, the calibration position identification marks 3 are arranged repeatedly 10000 times at a pitch interval of 200 nm, each having a rectangular cross section of a length of 1 mm in the depth direction, a width of 50 nm, and a height of 50 nm.

When this standard component for calibration is used for calibration in the electron-beam metrology system, there occurs a case where the plurality of calibration position identification marks 7 are included in its visual field depending on the scale factor at which the calibration position is identified. For example, in the case where the visual field in the scale factor specifying the calibration position is within 400 nm square, only one calibration position identification mark is viewable in the visual field; therefor, even when the calibration position identification marks are repeatedly arranged in the same form, the calibration shown in the first embodiment is possible. On the other hand, in the case where the visual field in the scale factor at which the calibration position is identified is 400 nm square or more, two or more calibration position identification marks can be seen in the visual field; therefore, if the calibration position identification marks are repeatedly arranged in the same form, it becomes difficult to discriminate which mark is for the desired position coordinates. In this case, a criterion of discrimination is dependent on the position accuracy of the stage. That is, with a system whose position accuracy of the stage is worse than about 200 nm, discrimination of the mark cannot be done.

In order to solve this problem, there is a method for designing the interval between marks to be more than or equal to a visual field range at a calibration position identification scale factor. On the contrary, if the interval between the marks is widened, there are problems: the total number of the marked locations is lessened and the locations to be used for the calibration are decreased in number; and when the location is first moved to the target position, the mark cannot be found and re-movement is repeated, and it takes a time to identify the position, etc. Thus, in the case of the calibration position identification mark arranged repeatedly in the same form of FIG. 1, a limit arises in a mark design depending on the scale factor at which the calibration position is identified and stage accuracy of the system.

Figure 10:
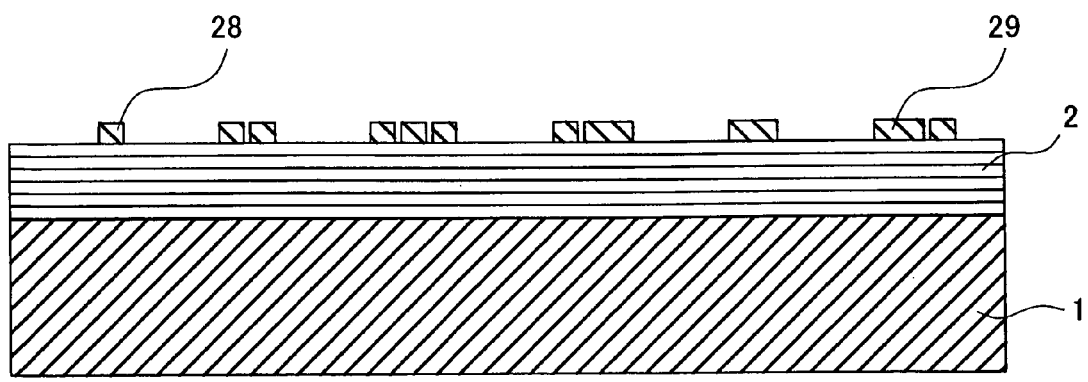
FIG. 10 is a cross section for explaining another construction example of the standard component for calibration of the present invention.

In order to solve these problems, the mark of a cross section shape as shown in FIG. 10 was produced. As shown in FIG. 10, as the calibration position identification mark, a rectangular cross section 28 of a length in the depth direction of 1 mm, a height of 50 nm, a pitch interval of 200 nm, and a width of 25 nm is increased from one to three sequentially on the multi-layer surface. Further with a combination of the rectangular cross section 28 of 25 nm width and a rectangular cross section 29 of 35 nm width, six or more kinds of the marks different in the number of mark elements and the width of the mark are arranged repeatedly 1000 times.

As a result, in the mark arrangement, since the mark in the same form is not seen within 1.2 µm, limitation by the scale factor at which the calibration position is identified and the stage accuracy of the system is mitigated largely.

Figure 11:
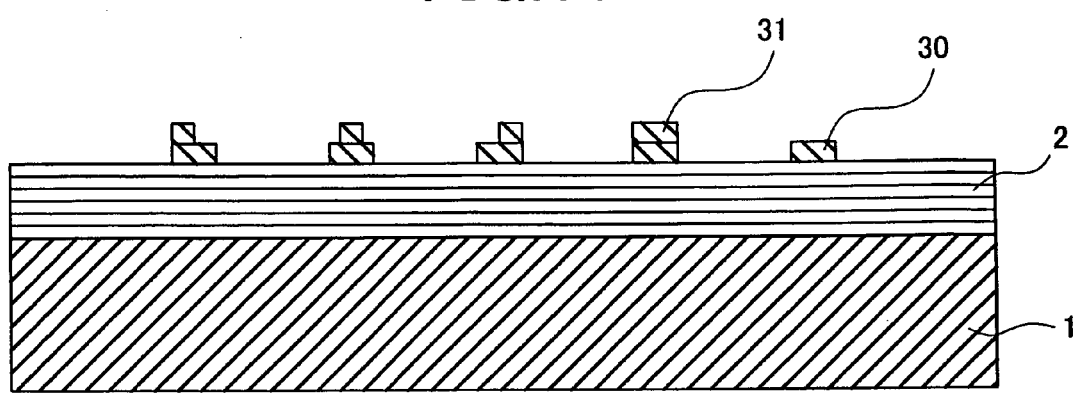
FIG. 11 is a cross section for explaining further another construction example of the standard component for calibration of the present invention.

Similarly, as shown in FIG. 11, the same effect can be attained by changing the cross section shape of the multi-layer surface. Details of the form will be explained. Calibration position identification marks 30, 31 are produced by superposing two layers of rectangle cross sections of a pitch interval of 200 nm and of a width of 0 nm to 50 nm, each rectangle cross section having a length in the depth direction of 1 mm and a height of 25 nm, on the multi-layer surface. Assuming that the width of the lower layer 30 is 50 nm and the width of the upper layer 31 is 25 nm, there are three kinds of lamination: a position of the upper layer is right end, center, and left end to the lower layer. Considering that the width of the upper layer takes 0 nm and 50 nm in addition to 25 nm, five or more kinds of the marks 30, 31 different in the cross section can be formed. Furthermore, if the kind of width is increased, it will be possible to increase the kind of mark shape easily.

As described above, according to the present invention, check of the superlattice position used for the calibration becomes easy by arranging the identification mark showing the calibration position in proximity of the superlattice. Moreover, regarding the identification mark that shows the calibration position, its absolute pitch size is given by the optical diffraction method, and therefore, it becomes possible to attain linewidth calibration in a direction perpendicular to the superlattice pitch direction simultaneously. Moreover, by making the identification mark that shows the calibration position with a metal, detecting the mark in the electron-beam system and detecting the mark of the cut-out position identification in the electron-beam system can be performed easily.

Thus, since the superlattice that shows the calibration position can be arranged adjacent to the superlattice, high-accuracy calibration becomes possible and high-accuracy metrology corresponding to the next-generation semiconductor processing can be realized.

What is claimed is:

1. A standard component for calibration for performing scale-factor calibration of an electron-beam system based on secondary charged particles detected by irradiation of a primary electron beam emitted from the electron-beam system on a substrate having a cross section of a superlattice pattern of a multi-layer structure in which different materials are deposited alternately, wherein the substrate has linear patterns that are on a substrate surface parallel to the multi-layer and are arranged at a fixed interval in a direction crossing the cross section of the superlattice pattern, and is so configured that the cross section of the linear pattern may exist on substantially the same plane of the superlattice cross section, so that the linear patterns enable a position of the superlattice pattern to be identified.

2. The standard component for calibration according to claim 1,
wherein each of the linear patterns is a linear pattern group of at least one or more linear pattern elements and is a linear pattern whose line pattern elements are different in number between the adjacent linear pattern groups that are arranged at a fixed interval.

3. The standard component for calibration according to claim 1,
wherein each of the linear patterns is the linear pattern group of at least one or more line pattern elements and is a linear pattern whose cross section shape is different between the adjacent linear patterns.

4. The standard component for calibration according to claim 1,
wherein the substrate contains a semiconductor material and the linear pattern is made up of any one of metal materials of aluminum (Al), tungsten (W), tantalum (Ta), molybdenum (Mo), and copper (Cu).

5. The standard component for calibration according to claim 1,
wherein the multi-layer interlayer pitch size of the multi-layer structure of different materials is less than or equal to 50 nm.

6. A standard component for calibration for performing scale-factor calibration of an electron-beam system based on secondary charged particles detected by irradiation of a primary electron beam emitted from the electron-beam system on a substrate having a cross section of a superlattice pattern of a multi-layer structure in which silicon layer and molybdenum layer are deposited alternately, wherein the substrate has linear tungsten patterns that are on a substrate surface parallel to the multi-layer and are arranged at a fixed interval in a direction crossing the cross section of the superlattice pattern, and is so configured that the cross section of the linear tungsten pattern may exist on substantially the same plane of the superlattice cross section, so that the linear tungsten patterns enable a position of the superlattice pattern to be identified.

7. A method for producing a standard component for calibration, comprising the steps of:

forming a substrate that has a cross section of a superlattice pattern of a multi-layer structure in which different materials are deposited alternately;

forming linear patterns arranged at a fixed interval in a direction crossing the cross section of the superlattice pattern on a surface of the multi-layer structure using lithography and an etching method; and forming the cross sections of the linear patterns so as to exist on substantially the same plane of the multi-layer cross section of the superlattice pattern.

8. The method for producing the standard component for calibration according to claim 7,
wherein the step of forming the cross section of the linear pattern uses either a cutting-out method using cleavage of the substrate of the multi-layer structure or a cutting-out method using an ion beam.

9. The method for producing a standard component for calibration according to claim 7,
wherein the substrate of the multi-layer structure contains a semiconductor material and the linear pattern is made up of any one of metal materials of aluminum (Al), tungsten (W), tantalum (Ta), molybdenum (Mo), and copper (Cu).

10. The method for producing the standard component for calibration according to claim 8, comprising a step of, when forming the linear pattern, forming a pattern for alignment around the perimeter of the linear pattern by lithography and by an etching method, wherein a cross section of the linear pattern is cut out with respect to the pattern for alignment.

11. An electron-beam system, comprising:

an irradiation optics for irradiating a primary electron beam emitted from an electron gun onto a sample mounted on a sample stage and scanning it;

a detector for secondary electrons or reflected electrons generated by the irradiation of the primary electron beam;

signal processing means for measuring the length of the sample by processing an electron signal obtained from the detector; and a standard component for calibration used to calibrate a scale factor of the irradiation optics from information of the intensity of the secondary electrons or reflected electrons;

wherein the standard component for calibration has a substrate that has a cross section of a superlattice pattern of a multi-layer structure in which different materials are deposited alternately and linear patterns that are on the substrate surface parallel to the multi-layer and are arranged at a fixed interval in a direction crossing the cross section of the superlattice pattern, and is so configured that a cross section of the linear pattern may exist on substantially the same plane of the superlattice cross section, so that the linear patterns enable a position of the superlattice pattern to be identified.

12. The electron-beam system according to claim 11, wherein the multi-layer interlayer pitch size of the superlattice pattern in the standard component for calibration and the pitch size of the linear patterns arranged at a fixed interval are found by an X-ray or optical diffraction method.

13. The electron-beam system according to claim 11, wherein the standard component for calibration is mounted on the sample stage.

* * * * *